United States Patent [19]

Schneider et al.

[11] 4,105,671
[45] Aug. 8, 1978

[54] INSECTICIDAL N-METHYLPYRROLIDINONYLACETANILIDES

[75] Inventors: Louis Schneider, Elizabeth; David E. Graham, Westfield, both of N.J.

[73] Assignee: GAF Corporation, New York, N.Y.

[21] Appl. No.: 796,520

[22] Filed: May 13, 1977

[51] Int. Cl.² ............................................. C07D 207/26
[52] U.S. Cl. ............................ 260/326.43; 260/313.1; 424/274
[58] Field of Search .................. 260/326.43; 424/274; 71/95

[56] References Cited

U.S. PATENT DOCUMENTS

| | | | |
|---|---|---|---|
| 3,769,301 | 8/1973 | Olin | 260/326.45 |
| 4,021,224 | 5/1977 | Pallos et al. | 71/88 |

*Primary Examiner*—Donald G. Daus
*Assistant Examiner*—Lisa Jones

*Attorney, Agent, or Firm*—Walter C. Kehm; Walter Katz

[57] ABSTRACT

Insecticidal N-acyl-N-(N'-methylenepyrrolidonyl)-dialkylanilines having the formula:

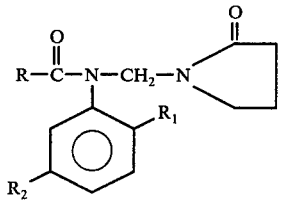

where $R_1$ and $R_2$ are both lower alkyl, and R is alkyl, alkenyl or haloalkenyl.

are prepared by two-step process involving reaction of 2,5-dialkylaniline with N-methylolpyrrolidone followed by acylation.

The compounds of the present invention show good insecticidal activity against the Mexican bean beetle.

5 Claims, No Drawings

INSECTICIDAL N-METHYLPYRROLIDINONYLACETANILIDES

BACKGROUND OF THE DISCLOSURE

1. Field of the Invention

This invention relates to novel N-(acyl)-N-(N'-methylenepyrrolidonyl)-2,5-dialkylanilines which are useful as insecticides.

2. Description of the Prior Art

U.S. Pat. No. 3,769,301 describes related N-(acyl-tertiaryamidoalkyl) acetanilides, including N-methylenepyrrolidonyl derivatives, however, these compounds are described as being herbicidially active only.

SUMMARY OF THE INVENTION

The present invention provides insecticidal N-acyl-N-(N'-methylenepyrrolidonyl)-2,5-dialkylanilines having the formula:

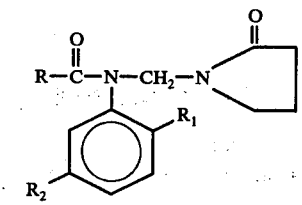

where $R_1$ and $R_2$ are both lower alkyl, and R is alkyl, alkenyl or haloalkenyl.

Suitably, R has from 2-12 carbon atoms, and the preferred compounds of the present invention are those in which $R_1$ and $R_2$ are both methyl, and R is undecanyl, $\alpha,\beta,\beta$-trichlorovinyl, or 9-decenyl.

The compounds of the present invention show good insecticidal activity, particularly against the Mexican bean beetle.

The novel compounds of the invention are prepared by two-step process involving reaction of 2,5-dialkylaniline with N-methylolpyrrolidone followed by acylation.

DETAILED DESCRIPTION OF THE INVENTION

The starting material N-methylolpyrrolidone is prepared by condensation by 2-pyrrolidone with paraformaldehyde in basic solution. The acylation reaction is carried out by refluxing 2,5 dimethylaniline with N-methylolpyrrolidone under azeotropic conditions in the presence of neutral alumina in a suitable solvent, while removing the stoichiometric amount of water from the reaction mixture. The intermediate product, N-(N'-methylenepyrrolidonyl)-2,5-dimethylaniline is isolated by crystallization from solution. This intermediate in turn is reacted with an acid chloride to provide the desired N-acyl-N-(N'-methylolpyrrolidonyl)-2,5-dialkylaniline. In a typical example, dodecanoyl chloride is the acylating agent.

The materials of the present invention may be applied to those insect susceptible plants on the site at a rate of about 1 or less to about 25 pounds per acre, or as a foliar dust or spray at concentrations of about 31 to 260 ppm, depending on various circumstances of the susceptibility of the insects, the weather, the stage of growth and various other factors. The material may be applied as a dust or spray. As a dust, it is more practical to extend it with diluents such as bentonite, chalk, clay, diatomaceous earth, fullers earth, mica, ground slate or any of the other usual carriers for agricultural chemicals. As a spray, it may be incorporated into water as a solution. The higher molecular weight compounds may be dissolved first in a solvent, such as an alcohol, or a petroleum fraction, such as isoparaffinic hydrocarbons, naphtha or kerosene, which may be dissolved in a suitable solvent and fogged or sprayed without water. Usually it is desirable to incorporate emulsifying agents and other wetting agents to insure complete contact with the insect.

Following are examples of preparation of the compounds of the invention, and are presented by way of illustration and are not intended to be limiting unless otherwise specified.

N-Dodecanoyl-N-(N'-Methylenepyrrolidonyl)-2,5-Dimethylaniline

EXAMPLE 1

N-Methylolpyrrolidone 2-pyrrolidone (212.4g. 2.0 mole) and potassium hydroxide (0.6g) is heated to 80° C. and paraformaldehyde (75.6g., 2.5 mole) is added during 10 minutes, and the mixture maintained at 75°–80° C. for ½ hr. The desired product then is crystallized from 1 part of benzene to yield 227g. (88.2%), m.p. 78°–80° C. of product.

N-(N'-Methylenepyrrolidonyl)-2,5-Dimethylaniline 2,5-Dimethylaniline (175g., 1.4 mole), xylene (300 cc), N-methylopyrrolidone (166.3g, 1.4 mole) and neutral alumina (100g) are refluxed under azeotropic conditions until the stoichiometric amount of water is removed. The alumina then is filtered off and the product is crystallized from xylene, slurried twice in hexane, and vacuum dried, to yield 203g. (64.4%), m.p. 109°–110° C. of product. Anal. Calcd for $C_{13}H_{18}N_2O$: N 12.83 Found: N, 12.61:

N-Methylenepyrrolidonyl-2,5-dimethylaniline (21.8g, 0.1 mole), dichloromethane (125 cc) and N,N-diisopropylethylamine (14.2g, 0.11 mole) are cooled to 5° C., and dodecanoylchloride (24.0g., 0.11 mole) in dichloromethane (25 cc) is added during ¼ hr. The reaction mixture is stirred at 0°–5° C. for 3 hrs., left overnight at ambient temperature, washed with 100 cc of cold water, 150 cc of 10% potassium bicarbonate, 150 cc of 5% hydrochloric acid, and finally 100 cc of water. The dichloromethane is removed by rotoevaporation and the desired product is crystallized from ether, to yield 24.5g. (64.4%) m.p. 81°–82° C. of product.

Anal. Calcd for $C_{25}H_{40}N_2O_2$: N, 6.99; Found: N, 7.20.

EXAMPLE 2

N-$\alpha,\beta,\beta$-Trichloroacryloyl-N-(N'-Methylenepyrrolidonyl)-2,5-Dimethylaniline N-Methylenepyrrolidonyl-2,5-dimethylaniline (21.8g., 0.1 mole), dichloromethane (125 cc) and N,N-diisopropylethylamine (14.2g, 0.11 mole) are cooled to 5° C., and trichloroacryloylchloride (21.3g., 0.11 mole) in dichloromethane (25 cc) is added during ¼ hr. The reaction mixture is stirred at 0°–5° C. for 3 hrs., left overnight at ambient temperature, washed with 100 cc of cold water, 150 cc of 10% potassium bicarbonate, 150 cc of 5% hydrochloric acid, and finally 100 cc of water. The dichloromethane is removed by rotoevaporation and the desired product crystallized from ether to yield 30.0g (80%) of a liquid product.

Anal. Calcd for $C_{16}H_{17}Cl_3N_2O_2$: N, 7.46; Found: N, 7.69.

EXAMPLE 3

N-10-Undecenoyl-N-(N'-Methylenepyrrolidonyl)-2,5-Dimethylaniline

N-Methylenepyrrolidonyl-2,5-dimethylaniline (21.8g., 0.1 mole), dichloromethane (125 cc) and N,N-diisopropylethylamine (14.2g., 0.11 mole) 10-undecenoyl chloride (22.3g., 0.11 mole) in dichloromethane (25 cc) is added during ¼ hr. The reaction mixture is stirred at 0°–5° C. for 3 hrs., and left overnight at ambient temperature, washed with 100 cc of cold water, 150 cc of 10% potassium bicarbonate, 150 cc of 5% hydrochloric acid, and finally 100 cc of water. The dichloromethane is removed by rotoevaporation and the desired product crystallized from ether to yield 23.0g (59.8%) m.p. 64°–65° C. of product.

Anal. Calcd for $C_{24}H_{36}N_2O_2$: N, 7.29; Found: N, 7.36.

EXAMPLE 4

The products of Examples 1–3 were tested for insecticidal activity against Mexican bean beetle as follows: a combination of stomach poison and feeding deterrent effects was measured on larvae of the Mexican bean beetle about 5 to 7 days after their emerging from eggs. Leaves of young bean plants were removed from the plants by cutting the petioles and were dipped in a suspension of the chemical at 250 ppm in the primary tests. Petioles of the excised leaves were placed in a water reservoir to maintain leaf turgidity and 5 larvae were placed upon them as soon as the chemical deposit was dry. Observations were made on the mortality of the beetles and the extent of inhibition of feeding 2 or 3 days later. The two responses were rated 0 (no effect on mortality or feeding) to 10 (complete destruction of larvae and total inhibition of feeding) against leaves dipped in a commercial standard, namely, Azodrin, which is 0,0-dimethyl-0-(2-methyl carbamoyl-1-methylvinyl) phosphate.

| INSECTICIDAL ACTIVITY | | | | |
|---|---|---|---|---|
| Conc., ppm | Compound of Example 1 | 2 | 3 | Azodrin |
| 250 | | 9 | 9 | 10 | 10 |

While the invention has been described with particular reference to certain embodiments thereof, it will be understood that certain modifications and changes may be made which are within the skill of the art. Therefore it is intended to be bound only by the appended claims.

What is claimed is:

1. Insecticidal N-acyl-N-(N'-methylenepyrrolidonyl)-2,5 dialkylanilines having the formula:

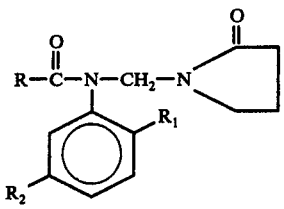

where $R_1$ and $R_2$ are both lower alkyl, and R is selected from alkyl, alkenyl and haloalkenyl having from 2 to 12 carbon atoms.

2. A compound according to claim 1 wherein both $R_1$ and $R_2$ are methyl.

3. A compound according to claim 1 which is N-dodecanoyl-N-(N'-methylenepyrrolidonyl)-2,5-dimethylaniline.

4. A compound according to claim 1 which is N-α,β,β-trichloroacryloyl-N-(N'-methylenepyrrolidonyl)-2,5-dimethylaniline.

5. A compound according to claim 1 which is N-10-undecenoyl-N-(N'-methylenepyrrolindonyl)-2,5-dimethylaniline.

* * * * *